(12) United States Patent
Yeo et al.

(10) Patent No.: US 11,660,253 B2
(45) Date of Patent: May 30, 2023

(54) DEVICE FOR EXTRACTING PLATELET RICH PLASMA

(71) Applicant: MEDISARANG CO., LTD., Gyeonggi-do (KR)

(72) Inventors: Seong-il Yeo, Gyeonggi-do (KR); Edouard Broussalian, Geneva (CH)

(73) Assignee: MEDISARANG CO., LTD., Gyeonggi-Do (KR)

( * ) Notice: Subject to any disclaimer, the term of this patent is extended or adjusted under 35 U.S.C. 154(b) by 815 days.

(21) Appl. No.: 16/574,159

(22) Filed: Sep. 18, 2019

(65) Prior Publication Data

US 2021/0077352 A1  Mar. 18, 2021

(51) Int. Cl.
*A61J 1/20* (2006.01)
*B04B 5/04* (2006.01)
*B04B 11/04* (2006.01)
*C12N 5/078* (2010.01)

(52) U.S. Cl.
CPC ........... *A61J 1/2096* (2013.01); *B04B 5/0407* (2013.01); *B04B 11/04* (2013.01); *C12N 5/0644* (2013.01)

(58) Field of Classification Search
CPC ...... A61J 1/2096; B04B 5/0407; B04B 11/04; C12N 5/0644; A61M 1/0272; A61M 1/029; A61M 2202/0427; B01L 2200/025; B01L 2200/026; B01L 2300/049; B01L 3/5021
USPC .......................................................... 494/16
See application file for complete search history.

(56) References Cited

FOREIGN PATENT DOCUMENTS

| KR | 1020110009651 | 1/2011 | |
|---|---|---|---|
| KR | 1010265990000 | 3/2011 | |
| KR | 1012673790000 | 9/2012 | |
| KR | 1020140135084 | 11/2014 | |
| KR | 1020150120840 | 10/2015 | |
| KR | 101666451000 | 10/2016 | |
| WO | WO-2017000851 A1 * | 1/2017 | .............. B01J 13/00 |

* cited by examiner

*Primary Examiner* — Shuyi S. Liu
(74) *Attorney, Agent, or Firm* — Stuart H. Mayer; Mayer & Williams PC

(57) ABSTRACT

The present invention relates to a platelet rich plasma (PRP) extracting device and extracting method using the same, and more particularly, to a platelet rich plasma (PRP) extracting device capable of quickly and effectively extracting the highly concentrated PRP from centrifuged blood by a simple manipulation.

7 Claims, 6 Drawing Sheets

DEVICE FOR EXTRACTING PLATELET RICH PLASMA

BACKGROUND

The present invention herein relates to a device for extracting platelet rich plasma and extracting method using the same.

When blood is centrifuged, the blood is separated into three layers. That is, red blood cells, which have heaviest specific gravity, are gathered in a lowest portion of a centrifuge tube, thereabove, platelets and leucocytes are gathered to form a thin layer, and solution elements including almost no particles are disposed thereabove. Here, an intermediate thin layer in which the platelets and the leucocytes are intensively gathered is referred to as platelet rich plasma (PRP), and, thereabove, a layer including only a solution without blood cell particles is referred to as platelet poor plasma (PPP). Originally, since the platelets contain various growth factors, the platelets play an important role for wound healing and skin regeneration. Also, it is reported that since the PRP contains platelets with a high concentration, the PRP exhibits effects in which various growth factors promote the proliferation of cells therearound and stimulate elements such as collagen to be well synthesized. Thus, in recent years, the PRP has been used in various fields including a pain treatment field such as backache and a skin disease field such as hair loss treatment, skin regeneration, or burn treatment. Although novel devices for a PRP extracting method are currently released, the devices have limitations in that red blood cells, which are intended to be excluded, are contained in an extract, and since an extraction process is extremely precise, the concentration of the PRP is not uniform to cause deviations in quality control. Furthermore, a conventional centrifuge tube for PRP extraction is extremely expensive. In relation to this, Korean Registered Patent No. 1267379 discloses a kit for separating blood.

SUMMARY

However, since the above-described related art is a technology for extracting a buffy coat that is a thin layer in which platelets and leucocytes are concentrated and which is disposed between plasma and a red blood cell layer, this technology is not appropriate for extracting only the PRP having a high concentration.

The present invention provides a device for extracting PRP and extracting method using the same, which is capable of quickly and effectively extracting the PRP having a high concentration from centrifuged blood through a simple manipulation. However, this may be merely illustrative, and thus the present invention is not limited thereto.

According to an aspect of the present invention, provided is a device for extracting platelet rich plasma (PRP), the device including: a main body unit including an upper accommodation space having a lower end portion having an inclined surface having a width gradually decreasing in a downward direction, a lower accommodation space disposed below the upper accommodation space and having an upper end portion having an inclined surface having a width gradually decreasing in an upward direction, and a bottleneck part that is a passage connecting the upper accommodation space and the lower accommodation space; an upper cover disposed above the main body unit and retractably coupled to the main body unit; and a lower cover disposed below the main body unit and retractably coupled to the main body unit to seal the lower accommodation space, wherein a syringe guide having a hollow tube structure, which extends downward from a protruding-type syringe insertion hole for inserting a syringe, and disposed inside the upper accommodation space is defined at a central portion of a top surface of the upper cover. Here, a syringe nozzle coupling hole having a protruding structure for being coupled with the syringe nozzle is defined at a position spaced apart from the syringe insertion hole, and a PRP extraction tube having a through hole structure, which extends downward from the syringe nozzle coupling hole in the upper accommodation space and having a lower inclined section, is disposed in the upper accommodation space. Also, when the upper cover descends, a lower end of the syringe guide blocks the bottleneck part and a space above the bottleneck part, and, at the same time, as the lower inclined section of the PRP extracting tube is inclined by contacting an inclined surface of the upper accommodation space, an end of the PRP extracting tube is partially closed and partially opened.

According to another aspect of the present invention, provided is a method of extracting platelet rich plasma from whole blood using the device of claim 1 comprising: injecting a whole blood collected from a subject into the device for extracting platelet rich plasma of claim 1; separating the whole blood into a plasma layer and a blood cell layer by centrifuging the device; rotating the upper cover of the device in order to lower the upper cover and to place a tip of the PRP extraction tube in the lower part of the plasma layer thereby; extracting the PRP using a syringe connected to the syringe nozzle coupling hole; and collecting extracted PRP.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Definition of Terms

Figure 1:
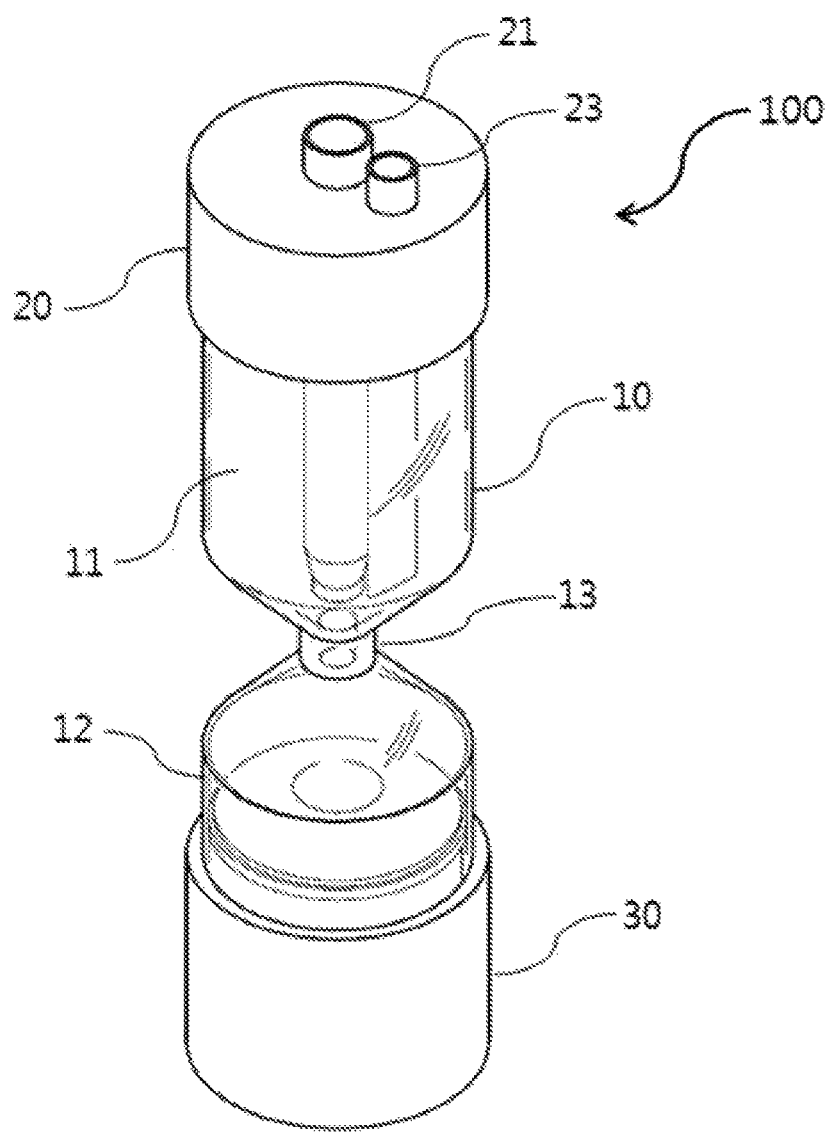
FIG. 1 is a schematic perspective view illustrating a device 100 for plasma extraction of the present invention.

A term of "platelet-rich plasma (PRP)" used in this specification refer to a concentrate obtained by extracting platelets from autologous blood. An intermediate thin layer in which platelets and leucocytes are intensively gathered when blood is centrifuged refers to PRP, and, thereabove, a blood layer consisting of only a solution without blood cell particles refers to platelet poor plasma (PPP).

A term of "luer activated valve (LAV)" used in this specification refers to a valve that is opened and closed in a variable manner according to a pressure applied from the outside. That is, the LAV refers to a valve having a structure in which while a shape of an inner silicon member is deformed when a pressure is applied to an upper portion of the valve, a fluid is movable from the outside to the inside or from the inside to the outside although a structure, in which the inner silicon member completely blocks the outside, is maintained.

Detailed Description

According to an aspect of the present invention, provided is a device for extracting platelet rich plasma (PRP), the device including: a main body unit including an upper accommodation space having a lower end portion having an inclined surface having a width gradually decreasing in a downward direction, a lower accommodation space disposed below the upper accommodation space and having an upper end portion having a width gradually decreasing in an upward direction, and a bottleneck part that is a passage connecting the upper accommodation space and the lower accommodation space; an upper cover disposed above the main body unit and retractably coupled to the main body unit; and a lower cover disposed below the main body unit and retractably coupled to the main body unit to seal the lower accommodation space, wherein a syringe guide having a hollow tube structure, which extends downward from a protruding-type syringe insertion hole for inserting a syringe, and disposed inside the upper accommodation space is defined at a central portion of a top surface of the upper cover. Here, a syringe nozzle coupling hole having a protruding structure for being coupled with the syringe nozzle is defined at a position spaced apart from the syringe insertion hole, and a PRP extraction tube having a through hole structure, which extends downward from the syringe nozzle coupling hole in the upper accommodation space and having a lower inclined section, is disposed in the upper accommodation space. Also, when the upper cover descends, a lower end of the syringe guide blocks the bottleneck part and a space above the bottleneck part, and, at the same time, as the lower inclined section of the PRP extracting tube is inclined by contacting an inclined surface of the upper accommodation space, an end of the PRP extracting tube is partially closed and partially opened.

In the device for extracting the PRP, the PRP extracting tube has a structure parallel to the syringe guide when the upper cover ascends. However, when the upper cover descends, the lower inclined section of the PRP extracting tube is inclined by contacting the inclined surface of the upper accommodation space and contacts the end of the syringe guide. Thus, a predetermined distance may be generated between the lower inclined section and the inclined surface.

In the device for extracting the PRP, when the upper cover ascends, the lower inclined section of the PRP extracting tube and the inclined surface of the upper accommodation space may have the same inclination angle, each of the syringe insertion hole and the syringe coupling hole of the upper cover may further include a cover capable of being selectively opened and closed, and forward and backward movements of the upper cover and the lower cover may be performed by rotating the upper cover and the lower cover.

In the device for extracting the PRP, the device may further comprise a luer activation valve connected to an upper portion of the syringe nozzle coupling hole.

In the device for extracting the PRP, wherein the luer activated valve may allow external fluid to be introduced to the inside when a shape of an inner silicon member is deformed by a pressure applied from the outside, but selectively blocks the introduction of the external fluid when the pressure is removed, and the shape of the silicon member is restored to an original shape.

According to another aspect of the present invention, provided is a method of extracting platelet rich plasma from whole blood using the device of claim 1 comprising: injecting a whole blood collected from a subject into the device for extracting platelet rich plasma of claim 1; separating the whole blood into a plasma layer and a blood cell layer by centrifuging the device; rotating the upper cover of the device in order to lower the upper cover and to place a tip of the PRP extraction tube in the lower part of the plasma layer thereby; extracting the PRP using a syringe connected to the syringe nozzle coupling hole; and collecting extracted PRP.

Hereinafter, preferred embodiments will be described in detail with reference to the accompanying drawings.

The present disclosure may, however, be embodied in many different forms and should not be construed as being limited to the embodiments set forth herein, rather, these embodiments are provided so that those skilled in the art thoroughly understand the present disclosure. Rather, these embodiments are provided so that this disclosure will be thorough and complete, and will fully convey the scope of the present disclosure to those skilled in the art. Also, in the figures, a thickness or dimension of each of layers is exaggerated for clarity of illustration.

The terms used herein are for illustrative purposes of the present disclosure only and should not be construed to limit the meaning or the scope of the present disclosure. As used in this specification, a singular form may, unless definitely indicating a particular case in terms of the context, include a plural form. Also, the expressions "comprise" and/or "comprising" used in this specification neither define the mentioned shapes, numbers, steps, operations, members, elements, and/or groups of these, nor exclude the presence or addition of one or more other different shapes, numbers, steps, operations, members, elements, and/or groups of these, or addition of these. The term "and/or" used herein includes any and all combinations of one or more of the associated listed items.

Hereinafter, embodiments of the present invention will be described with sectional views as ideal exemplary views of the present invention. In the drawings, for example, according to the manufacturing technology and/or tolerance, the modification of the illustrated shape may be expected. Thus, the exemplary embodiments of the present disclosure must not be interpreted to be limited by a particular shape that is illustrated in the drawings and must include a change in the shape occurring, for example, during manufacturing.

Hereinafter, the present invention will be described in more detail through embodiments. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

The inventors have developed a bio-device (Korean Registered Patent No. 1049201) for extracting a haematopoietic stem cell and a mesenchymal stem cell in peripheral blood. This bio-device may easily separate and extract a typical buffy coat layer including a stem cell in blood. However, this invention provides a device for extracting the buffy coat that is a transparent layer exactly distinguished after centrifugation. Thus, in order to extract platelet rich plasma (PRP) disposed below a plasma layer and distinguished from the buffy coat, a novel device is required. In case of a typical commercialized extracting device for PRP extraction, red blood cells, which are intended to be excluded, are contained in an extract. Also, since an extraction process is extremely precise, a concentration of the PRP is not uniform according to extractors to cause a deviation in quality control. Furthermore, since the extraction process requires a delicate manipulation, much time is consumed, and a concentration of the extracted PRP is hardly adjusted from a high concentration to a low concentration. The inventors have complete the present invention in order to resolve above-described limitations by adding a PRP extracting tube for extracting only PRP to the bio-device and developing a device 100 for extracting the PRP, which is capable of quickly and effectively extracting the highly concentrated PRP.

FIG. 1 is a schematic perspective view illustrating a shape of a device 100 for extracting the PRP of the present invention. As illustrated, the device 100 for extracting the PRP (hereinafter, referred to as the "PRP extracting device 100") of the present invention may be largely divided into a main body unit 10, an upper cover 20, and a lower cover 30. Particularly, the main body 10 includes an upper accommodation space 11, a lower accommodation space 12 disposed below the upper accommodation space 11, and a bottleneck part 13 connecting the upper accommodation space 11 to the lower accommodation space 12. In the main body unit 10, a lower end portion of the upper accommodation space 11 has a shape of which a width gradually decreases in a downward direction, and an upper portion of the lower accommodation space 12 has a shape of which a width gradually decreases in an upward direction. Also, the upper cover 20 retractably coupled to the main body unit 10 along a screw thread (not shown) provided on a surface is provided at an upper portion of the upper accommodation space 11, and the lower cover 30 coupled to the main body unit 10 along the screw thread provided on the surface is provided at a lower portion of the lower accommodation space 12.

Although each of a syringe insertion hole 21 and a syringe nozzle coupling hole 23 of the upper cover 20 has an opened shape in FIG. 1, a separate cover for selectively opening and closing an upper portion of each of the syringe insertion hole 21 and the syringe nozzle coupling hole 23 may be provided for pollution prevention of a sample and quickness of work. Also, the upper cover 20 in which a syringe guide 22 and a platelet rich plasma extracting tube 24 are provided may be manufactured to have a shape in which the syringe guide 22 and the platelet rich plasma extracting tube 24 are capable of being coupled to or separated from the upper cover. The present invention has a technical feature of quickly extracting the PRP according to adjustment of the PRP extracting tube 24, and description for this will be described in detail in FIG. 2.

Figure 2:
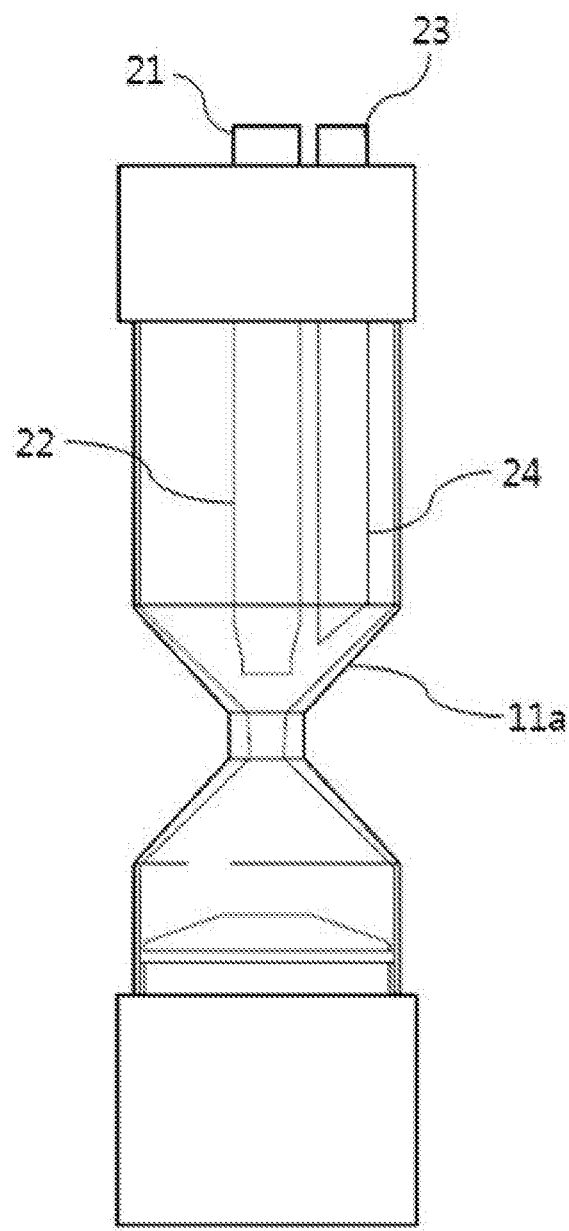
FIG. 2 is a schematic front view illustrating an inner structure of an upper accommodation space 11 of the device 100 for plasma extraction of the present invention.

FIG. 2 is a schematic front view illustrating an inner structure of the upper accommodation space 11 of the PRP extracting device 100 of the present invention. The protruding-type syringe insertion hole 21 for inserting a syringe into the main body unit 10 is defined at a central portion of a top surface of the upper cover 20, and the syringe guide 22 is provided to have a hollow tube structure, which extends downward from the upper cover 20 along the syringe insertion hole 21 so that the syringe is disposed inside the upper accommodation space 11. Here, when the upper cover 20 descends, a lower end of the syringe guide 22 may block the bottleneck part 13 and a space above the bottleneck part 13. Also, the protruding-type syringe nozzle coupling hole 23 capable of being coupled with the syringe nozzle for extracting the PRP and having a size less than that of the syringe insertion hole 21 is defined next to the syringe insertion hole 21 of the upper cover. Here, the PRP extracting tube 24 having a hollow tube structure, which extends downward from the upper cover 20 along the syringe nozzle coupling hole 23, is disposed in the upper accommodation space 11 in the form of a 11-shape in parallel to the syringe guide 22.

Also, when the upper cover 20 rotates to the right, the syringe guide 22 moves downward to block an upper portion of the bottleneck part 13, and when the upper cover 20 rotates to the left, the syringe guide 22 moves upward to open the upper portion of the bottleneck part 13. According to an operation principle of the syringe guide 22, as the lower cover 30 rotates to the right to move the lower cover 30 upward after blood is centrifuged, the buffy coat layer disposed in the lower accommodation space 12 may be positioned at the bottleneck part 13, and then the syringe guide 22 may move to block the upper portion of the bottleneck part 13 by rotating the upper cover 20 to the right. Thereafter, the syringe may be inserted into the syringe guide 22 to collect only the buffy coat layer of the bottleneck part 13. Also, the PRP extracting tube 24, which passes through the upper cover 20 along the syringe nozzle coupling hole 23 and extends downward to be disposed in the upper accommodation space 11, may operate like the syringe guide 22. That is, the PRP extracting tube 24 may move upward or downward by adjusting the upper cover 20. Here, due to a lower inclined section shape of the end of the PRP extracting tube 24 and a structure of an inclined surface 11a of the upper accommodation space, in which the lower end portion of the upper accommodation space has a width gradually decreasing in a downward direction, the buffy coat layer and the PRP layer may be sequentially extracted. In the above description, in order to easily describe the operation principle of the PRP extracting device 100 of the present invention, although the movement of each of the syringe guide 22 and the PRP extracting tube 24 according to the rotation of each of the upper cover 20 and the lower cover 30 is specified to the right or left direction, this may be changed or adjusted in manufacturing according to convenience of a user. For example, each of the syringe guide 22 and the PRP extracting tube 24 moves downward when the upper cover rotate to the left and moves upward when the upper cover rotates to the right.

Figure 3:
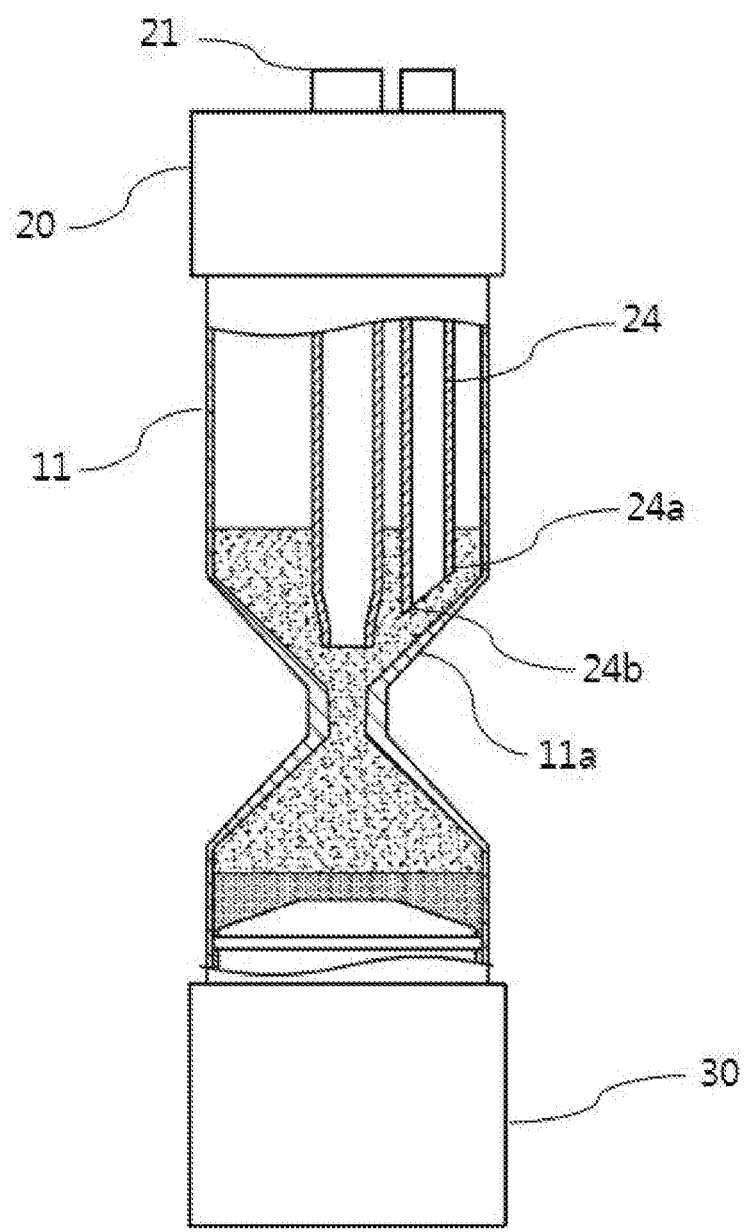
FIG. 3 is a cross-sectional view illustrating a state in which a blood sample is accommodated in the device 100 for plasma extraction of the present invention.

FIG. 3 is a cross-sectional view illustrating a state in which a blood sample is accommodated in the PRP extracting device 100 of the present invention. When a process of collecting a blood sample is described in more detail, firstly, an anticoagulant is suctioned by a syringe before blood is collected. An appropriate amount of the anticoagulant is about 10% of an amount of the blood to be collected. Thereafter, blood is collected from a patient by using the syringe in which the anticoagulant is suctioned. After the blood of the patient is collected, the upper cover 20 of the PRP extracting device 100 of the present invention may be opened, and the blood may be injected into the main body unit 10 by the syringe, and the syringe from which a needle is removed may be inserted through the syringe insertion hole 21, and then the blood may be discharged to the lower end of the syringe guide 22 and injected to a direction toward the lower accommodation space 12 of the main body unit 10. Here, when the blood is injected into the PRP extracting device 100 in a state in which the lower end of the syringe guide closely contacts an upper end of the bottleneck part 13 of the main body unit 10 by rotating the upper cover 20 in one direction, since the inner space of the main body unit 10 is sealed, the blood injection may be hardly performed, and since the bottleneck part 13 is blocked by the lower end of the syringe guide 22, the injected blood may not move down to the lower accommodation space 12. Thus, when the blood is injected, the upper cover 20 may rotate by a predetermined amount in an opposite direction to secure a space between the syringe guide 22 and the bottleneck part 13, and when coupling between the upper cover 20 and the main body unit 10 is loosened, the blood injection may be smoothly performed, and the injected blood may move down to the lower accommodation space 12 through the bottleneck part 13.

When the blood sample is centrifuged, the blood sample is separated into a plasma portion, which is an uppermost layer, and a red blood cell layer, which is a lowermost layer, as described above. The buffy coat, which is a thin layer in which platelets and leucocytes are concentrated, is distributed at a boundary between the plasma and the red blood cell layer, and a PRP layer is distributed above the buffy coat.

The PRP extracting device 100 of the present invention is a device for effectively extracting PRP. Here, before a sample is extracted, the syringe guide 22 and the PRP extracting tube 24 form a parallel structure to each other. However, when the upper cover 20 rotates to the right, the syringe guide 22 and the PRP extracting tube 24 simultaneously move downward. When the upper cover 20 is in a state of being unable to rotate to the right (locked state), the syringe guide 22 blocks the upper portion of the bottleneck part 13, and as the lower inclined section of the PRP extracting tube 24 contacts the inclined surface 11a of the upper accommodation space, the shape of the PRP extracting tube 24 is inclined, and one surface of the lower inclined section contacts the syringe guide 22. Here, while a structure in which an end upper portion 24a of the PRP extracting tube 24 contacts the inclined surface 11a of the upper accommodation space, and an end lower portion 24b dose not contact the inclined surface 11a, is maintained, i.e., a predetermined distance between the lower inclined section and the inclined surface 11a is formed, the PRP is extracted through a syringe (not shown) coupled to the syringe nozzle coupling hole 23. The process of extracting the PRP will be described in detail in FIG. 4.

Figure 4:
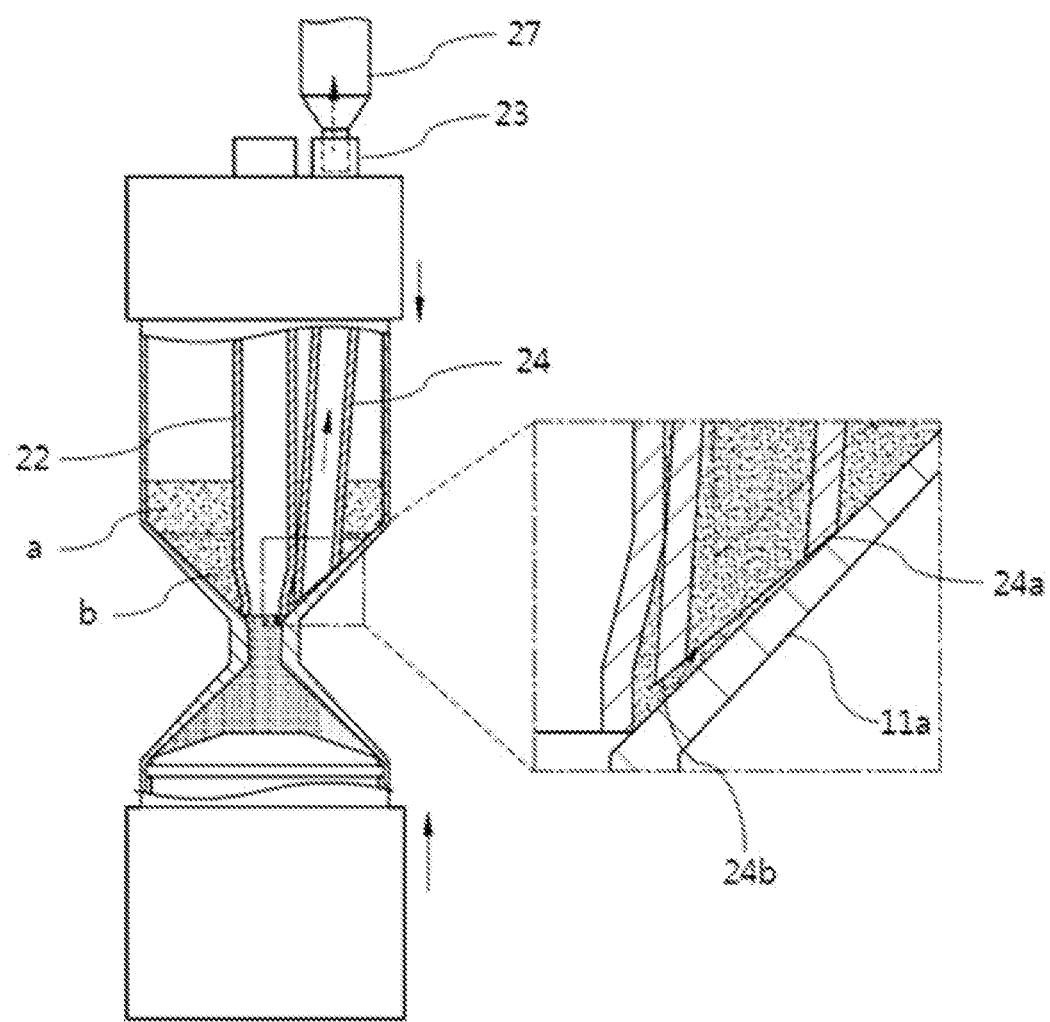
FIG. 4 is a schematic cross-sectional view illustrating a process of extracting platelet rich plasma (PRP) according to an operation of a platelet rich plasma extracting tube 24 of the device 100 for plasma extraction of the present invention.

FIG. 4 is a schematic cross-sectional view illustrating the process of extracting the PRP according to an operation of the PRP extracting tube 24 of the PRP extracting device 100 of the present invention. As illustrated, the blood sample is centrifuged, and then, as the upper cover 20 rotates to the right, the syringe guide 22 and the PRP extracting tube 24 move downward, and the syringe guide 22 completely blocks the upper portion of the bottleneck part 13. Also, as the PRP extracting tube 24 also moves downward, and the end of the PRP extracting tube 24 is pressed and inclined by contacting the inclined surface 11a, while one surface of the PRP extracting tube 24 contacts the syringe guide 22, the end upper portion 24a of the lower inclined section of the PRP extracting tube 24 having an inclined surface structure contacts the inclined surface 11a of the upper accommodation space, and as the end lower portion 24b is slightly spaced apart from the inclined surface 11a of the upper accommodation space, a gap through which the solution inside the upper accommodation space 11 flows into the PRP extracting tube 24 is generated. Here, when the syringe is coupled to the syringe nozzle coupling hole 23 defined in the upper cover 20, and then a negative pressure is applied, while a PRP layer (b) distributed around the PRP extracting tube 24 moves upward along the PRP extracting tube 24 inserted through the space, only the PRP may be effectively extracted through the syringe 27. Although, during the extraction process, a plasma layer (a) may be suctioned and extracted instead of the PRP layer (b), in general, when blood of 30 cc is centrifuged, PRP of 0.2 cc to 0.3 cc may be extracted. Thus, when extraction is performed until 0.3 cc on a scale of the syringe 27 having a volume of 1 cc and then the syringe is removed, only the highly concentrated PRP may be extracted without being mixed with the plasma layer (b), and thus a mixture may be prevented. Also, a final volume of the PRP may be selectively adjusted according to worker's know-how and the kind of disease.

Figure 5:
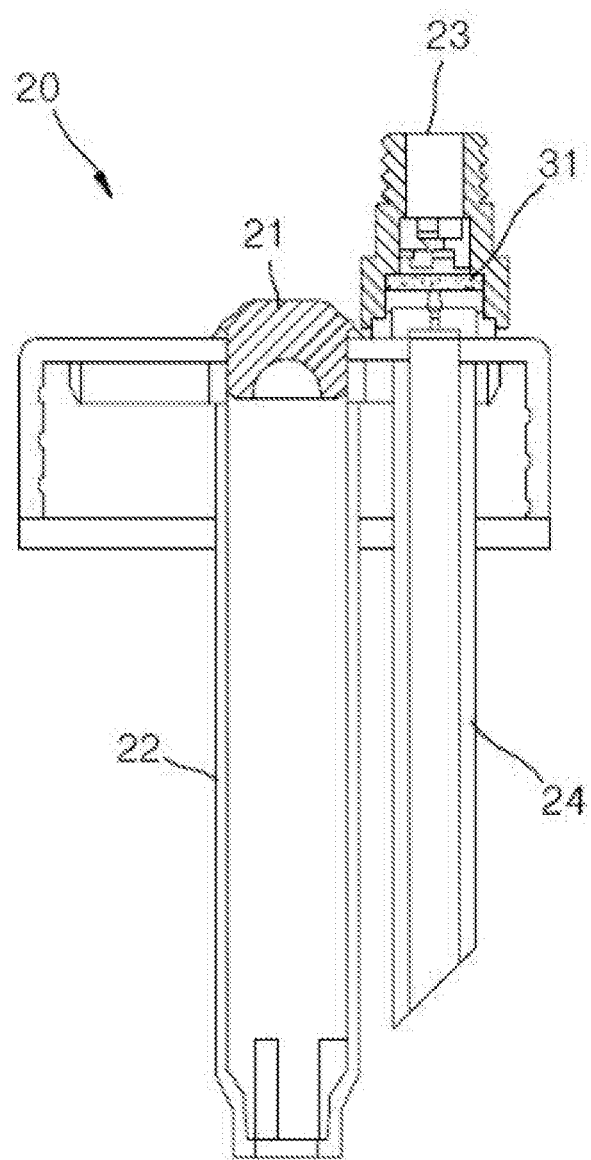
FIG. 5 is a schematic cross-sectional view illustrating a configuration including a luer activated valve 31 below the syringe nozzle coupling hole 23 of the PRP extracting device 100 of the present invention.
Figure 6:
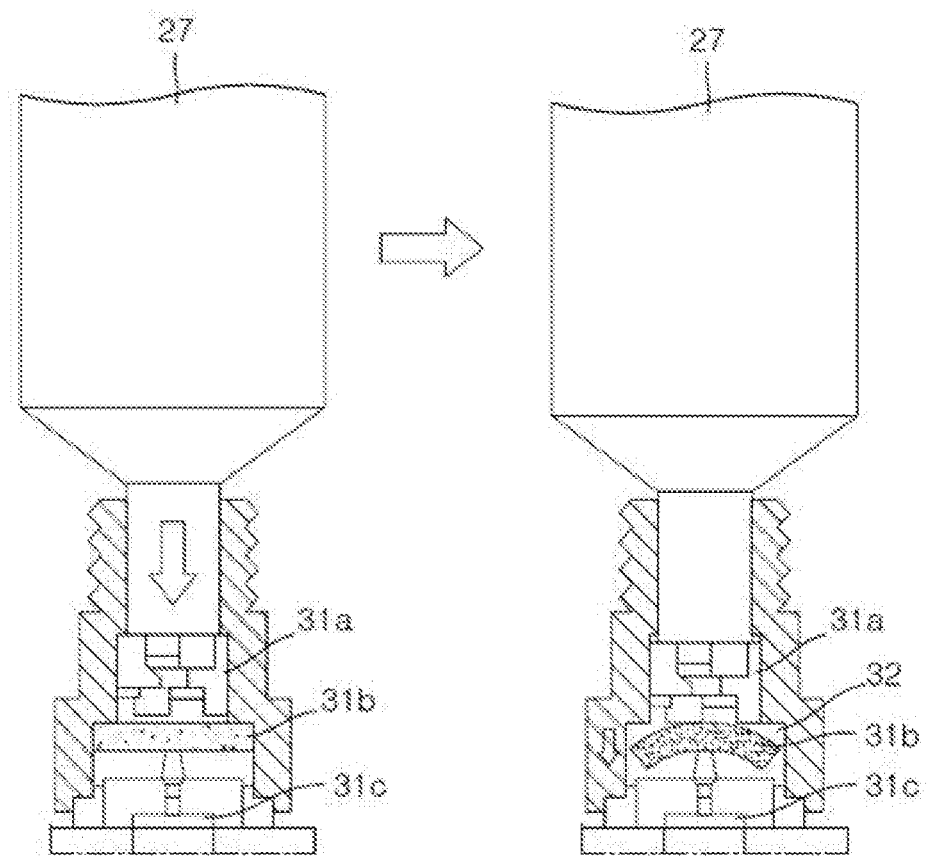
FIG. 6 is a schematic cross-sectional view illustrating the principle of the luer activated valve 31 of a device 100 for plasma extraction of the present invention.

FIG. 5 is a schematic cross-sectional view illustrating a configuration including a luer activated valve 31 below the syringe nozzle coupling hole 23 of the PRP extracting device 100 of the present invention. As illustrated, the syringe guide 22 provided downward along the syringe insertion hole 21 is disposed at the central portion of the upper cover 20, and the PRP extracting tube 24 provided downward along the syringe nozzle coupling hole 23 is disposed at the right side of the upper cover 20. As the luer activated valve 31 is provided below the syringe nozzle coupling hole 23, collected blood samples may be easily injected into the device and simultaneously the highly concentrated PRP may be easily collected. Typically, blood is collected from a patient, and then a needle of the syringe 27 is removed. Thereafter, a rubber stopper coupled to the syringe nozzle coupling hole 23 is opened, and the syringe is coupled to inject blood in the syringe 27 into the device. Then, centrifugation is performed. Thereafter, the PRP is collected by a negative pressure of the syringe 27 through the syringe nozzle coupling hole 23, and then the rubber stopper is coupled again. Thus, the above-described typical injection and collecting method has a limitation of being exposed to an external pollution source while the rubber stopper of the syringe nozzle coupling hole 23 is opened and closed. However, the PRP extracting device 100 of the present invention adopts the luer activated valve 31 below the syringe nozzle coupling hole 23 to minimize a possibility of a pollution source that may be generated while the blood sample is injected or the PRP is collected. A principle of this will be described in detail through FIG. 6. Firstly, since a silicon member 31b of the luer activated valve 31 completely blocks the upper portion in a state in which the syringe 27 is simply coupled to the syringe nozzle coupling hole 23, the blood sample may not be injected into the device. However, when the syringe 27 is slightly pushed downward, as an injection part 31a of the luer activated valve 31 moves down, and the silicon member 31b also moves down at the same time, a silicon support 31c is pressed, and a shape of the silicon member 31b is bent into an arch shape due to elasticity. Here, a drain hole 32 is generated in the inside, which completely blocks the upper portion, due to deformation of the silicon member 31b, and when the blood of the syringe 27 is injected, the blood, which has passed through the injection part 31a, flows to the PRP extraction tube 24 through the drain hole 32. Thereafter, when the syringe 27 is removed, while the injection part 31a ascends, the silicon member 31b is restored to an original shape to completely block the upper portion again. Likewise, even when the PRP is collected, in the same method as describe above, the PRP, which is disposed at a lower portion of the device, moves upward along the drain hole 32, which is defined by the deformation of the silicon member 31b, and moves into the syringe 27 to complete the PRP extraction.

As described above, the device for PRP extraction of the present invention may exhibit effects of being able to quickly and effectively extract the pure highly concentrated PRP excluding the buffy coat layer from the centrifuged blood through the simple manipulation by including the separate PRP extracting tube. However, the scope of the present invention is not limited to the above-described effects.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed. Hence, the real protective scope of the present invention shall be determined by the technical scope of the accompanying claims.

What is claimed is:

1. A device for extracting platelet rich plasma (PRP), the device comprising:
    a main body unit comprising an upper accommodation space having a lower end portion having an inclined surface having a width gradually decreasing in a downward direction, a lower accommodation space disposed below the upper accommodation space and having an upper end portion having a width gradually decreasing in an upward direction, and a bottleneck part that is a passage connecting the upper accommodation space and the lower accommodation space;
    an upper cover disposed above the main body unit and retractably coupled to the main body unit; and
    a lower cover disposed below the main body unit and retractably coupled to the main body unit to seal the lower accommodation space,
    wherein a syringe guide having a hollow tube structure, which extends downward from a protruding-type syringe insertion hole for inserting a syringe, and disposed inside the upper accommodation space is defined at a central portion of a top surface of the upper cover, wherein, a syringe nozzle coupling hole having a protruding structure for being coupled with a syringe nozzle is defined at a position spaced apart from the syringe insertion hole, and a PRP extraction tube having a through hole structure, which extends downward from the syringe nozzle coupling hole in the upper accommodation space and having a lower inclined section, is disposed in the upper accommodation space, wherein, when the upper cover descends, a lower end of a syringe guide blocks the bottleneck part and a space above the bottleneck part, and, at the same time, as a shape of the PRP extracting tube is inclined, and one surface of the lower inclined section contacts the syringe guide, while a structure in which an end upper portion of the PRP extracting tube contacts the inclined surface of the upper accommodation space, and an end lower portion does not contact the inclined surface is maintained.

2. The device of claim 1, wherein when the upper cover ascends, the lower inclined section of the PRP extracting tube and the inclined surface of the upper accommodation space have the same inclination angle as each other.

3. The device of claim 1, wherein each of the syringe insertion hole and the syringe coupling hole of the upper cover further comprises a cover that is selectively openable and closeable.

4. The device of claim 1, wherein forward and backward movements of the upper cover and the lower cover are performed by rotating the upper cover and the lower cover.

5. The device of claim 1, further comprising a luer activated valve connected to an upper portion of the syringe nozzle coupling hole.

6. The device of claim 5, wherein the luer activated valve allows external fluid to be introduced to the inside when a shape of an inner silicon member is deformed by a pressure applied from the outside, but selectively blocks the introduction of the external fluid when the pressure is removed, and the shape of the silicon member is restored to an original shape.

7. A method of extracting platelet rich plasma from whole blood using the device of claim 1 comprising:
    injecting a whole blood collected from a subject into the device for extracting platelet rich plasma of claim 1;
    separating the whole blood into a plasma layer and a blood cell layer by centrifuging the device;
    rotating the upper cover of the device in order to lower the upper cover and to place a tip of the PRP extraction tube in the lower part of the plasma layer thereby;
    extracting the PRP using a syringe connected to the syringe nozzle coupling hole; and
    collecting extracted PRP.

* * * * *